(12) United States Patent
Zhang et al.

(10) Patent No.: US 11,674,934 B2
(45) Date of Patent: Jun. 13, 2023

(54) METHODS OF COMPOSITIONAL ANALYSIS OF ALGAL BIOMASS

(71) Applicant: ExxonMobil Technology and Engineering Company, Annandale, NJ (US)

(72) Inventors: Anding Zhang, Short Hills, NJ (US); Kuangnan Qian, Skillman, NJ (US); Chengrong Wang, Easton, PA (US); Amy C. Clingenpeel, Washington, NJ (US)

(73) Assignee: EXXONMOBIL TECHNOLOGY AND ENGINEERING COMPANY, Annandale, NJ (US)

(*) Notice: Subject to any disclaimer, the term of this patent is extended or adjusted under 35 U.S.C. 154(b) by 339 days.

(21) Appl. No.: 17/142,786

(22) Filed: Jan. 6, 2021

(65) Prior Publication Data
US 2021/0262995 A1    Aug. 26, 2021

Related U.S. Application Data

(60) Provisional application No. 62/979,465, filed on Feb. 21, 2020.

(51) Int. Cl.
G01N 31/12    (2006.01)

(52) U.S. Cl.
CPC ....... *G01N 31/12* (2013.01); *G01N 2333/405* (2013.01)

(58) Field of Classification Search
CPC .................................................. G01N 31/12
USPC .......................................................... 436/155
See application file for complete search history.

(56) References Cited

U.S. PATENT DOCUMENTS

| | | | |
|---|---|---|---|
| 8,858,657 B1* | 10/2014 | Deng | C11C 3/003 44/388 |
| 2007/0196925 A1 | 8/2007 | Reischman | |
| 2015/0361371 A1* | 12/2015 | Hoekman | C10L 5/447 44/589 |
| 2017/0198223 A1* | 7/2017 | Chinnasamy | C10G 1/065 |

OTHER PUBLICATIONS

Varga, I. et al, Journal of Analytical Atomic Spectrometry 1999, 14, 881-883.*
Ross, A. B. et al, Bioresource Technology 2008, 99, 6494-6504.*
Morgan, T. J. et al, Energy & Fuels 2015, 29, 1669-1685.*

* cited by examiner

*Primary Examiner* — Arlen Soderquist
(74) *Attorney, Agent, or Firm* — Shook, Hardy & Bacon L.L.P.

(57) ABSTRACT

The present disclosure relates to methods for compositional analysis of algal biomass, specifically weight percent elemental composition. In at least one embodiment, a method for compositional analysis of an algae sample includes flash combusting a first portion of the algae sample to provide a carbon wt %, a hydrogen wt %, and a nitrogen weight %. The method includes pyrolysing a second portion of the algae sample to provide an oxygen wt %. The method includes scanning a third portion of the algae sample using x-ray fluorescence to provide an elemental intensity. The method includes normalizing the elemental intensity using the carbon wt %, the hydrogen wt %, the nitrogen wt %, and/or the oxygen wt %.

22 Claims, No Drawings

METHODS OF COMPOSITIONAL ANALYSIS OF ALGAL BIOMASS

CROSS-REFERENCE TO RELATED APPLICATIONS

This application claims the benefit of priority from U.S. Provisional Application No. 62/979,465 filed Feb. 21, 2020, which is hereby incorporated by reference in its entirety.

FIELD OF THE INVENTION

The present disclosure relates to methods for compositional analysis of algal biomass, specifically weight percent elemental composition.

BACKGROUND OF THE INVENTION

Recent emphasis on finding alternative energy sources to fuel the energy needs of the United States and the world is leading to an accelerated search for new fuels or new sources of fuel. Producing a liquid fuel from biomass, or biofuel, is an important focus of many alternative energy strategies.

Biofuels may be produced from terrestrial plants or from smaller organisms such as algae. It is advantageous to use algae for production of fuels because algae can produce 10 to 100 times as much mass as terrestrial plants in a year. With more than 100,000 known species of diatoms (a type of algae), 40,000 known species of green plant-like algae, and smaller numbers of other algae species, algae may grow rapidly in nearly any environment, with almost any kind of water, including marginal areas with limited or poor quality water.

Biofuels, such as biodiesel can be produced from lipid producing algae strains. Biodiesel is an alternative, non-toxic, biodegradable and renewable diesel fuel. These characteristics of biodiesel reduce the emission of carbon monoxide, hydrocarbons, and particulate matter in the exhaust gas compared to diesel fuel. In order to use algal biomass for production of biofuels, knowledge of the elemental composition is desired to aid in process and refining decisions.

While the compositional analysis of algal biomass is valuable, performing such analysis poses significant challenges because of the inherent heterogeneous nature of algal biomass. The heterogeneous nature of algal biomass means that the biomass does not readily dissolve in a single solvent and the high organic content makes acid digestion of the sample difficult. Conventional techniques require multiple separation steps before an analysis may be performed. For example, algal biomass may be quantitatively separated by dissolution with various solvent producing fractions such as non-polar lipids, polar lipids, salts, proteins, and carbohydrates. The separation requires multiple extraction steps and repeated solvent removal to provide quantitative data related to elemental composition of the overall sample. The process is lengthy and cost-inefficient. Another difficulty in determining elemental composition is provided by the high-salt content of algal biomass that is grown in salt-water. For example, a high salt content makes inductively coupled plasma, mass spectrometry, and atomic absorption spectroscopy challenging.

There is a need for improved methods for compositional analysis of algal biomass samples, including samples with high salt content. Additionally, there is a need for methods with reduced costs, and fewer steps while maintaining accuracy of elemental analysis results. References for citing in an information disclosure statement pursuant to (37 C.F.R. 1.97(h)) include: US 2007/0196925 A1

SUMMARY OF THE INVENTION

The present disclosure relates to methods for compositional analysis of algal biomass, specifically weight percent elemental composition.

In at least one embodiment, a method for compositional analysis of an algae sample includes flash combusting a first portion of the algae sample to provide a carbon wt %, a hydrogen wt %, and a nitrogen weight %. The method includes pyrolysing a second portion of the algae sample to provide an oxygen wt %. The method includes scanning a third portion of the algae sample using x-ray fluorescence to provide an elemental intensity. The method includes normalizing the elemental intensity using the carbon wt %, the hydrogen wt %, the nitrogen wt %, and/or the oxygen wt %.

In at least one embodiment, a method for compositional analysis of an algae sample includes drying the algae sample to produce a dried algae sample. The method includes flash combusting a first portion of the dried algae sample to provide a carbon wt %, a hydrogen wt %, and a nitrogen weight %. The method includes pyrolysing a second portion of the dried algae sample to provide an oxygen wt %. The method includes scanning a third portion of the dried algae sample for elemental intensity using x-ray fluorescence. The method includes normalizing the elemental intensity using the carbon wt %, the hydrogen wt %, the nitrogen wt %, and/or the oxygen wt %.

DETAILED DESCRIPTION OF THE INVENTION

Provided are methods for performing compositional analysis of algae samples. Methods may include sample preparation, including any of pretreatment, washing, dewatering, drying and/or lyophilization. Methods may also include flash combustion and/or pyrolysis of a portion of an algae sample to provide weight percent of elements such as carbon, nitrogen, hydrogen, and oxygen. Additionally, methods may include scanning a portion of the sample to provide elemental intensity using x-ray fluorescence to provide an elemental intensity and normalizing the elemental intensity using the weight percent of carbon, hydrogen, nitrogen, and oxygen. Methods can provide carbon and other elemental balances of biomass compound types, such as lipids, proteins and carbohydrates. The compositional information can be useful for assessing qualities of algae biomass and corresponding bio-fuel and bio-chemicals.

It has been discovered that the combination of quantitative analysis of carbon, hydrogen, nitrogen, and oxygen and x-ray fluorescence spectroscopy once normalized can provide compositional analysis of algal biomass without the need for multiple separation steps and repeated extractions with various solvents. Elemental composition may provide ratios of elements that can affect the decisions made in algal production methods. For example, a high nitrogen content may suggest that the algae is producing more protein than lipid and the feedstock or type of algae may be adjusted so the algal growth provides more lipids that may be converted into biodiesel. Additionally, knowledge of metal content could direct aid in refining the biofuel products.

Additionally, the combination of analysis techniques provides fast and accurate compositional analysis that covers almost the entire periodic table of the elements. Methods described provide advantages over prior processes in that the combination is less labor-intensive and more cost efficient. Additionally, the methods are suitable for use with various types of algal biomass including raw, lyophilized, and soxhleted/fractionated materials.

Optional Pretreatment

As an optional initial procedure an algae sample can be washed with water prior to drying. The water wash may be performed at ambient temperature and pressure, or at least one of the temperature or pressure can be elevated relative to ambient conditions. This optional process can remove at least a portion of ionic impurities (e.g. salts) or other non-algae compounds present in the algae sample.

Algae are typically grown in an aqueous environment that contains a variety of water soluble metal salts, including NaCl. When algae sample is taken, typically a portion of the algal culture medium is harvested with the algae sample. Performing an initial water wash of an algae sample allows at least a portion of such metal salts to be removed from the algae feed prior to introducing an extraction solvent. This reduces the amount of impurities that are inadvertently included in the elemental analysis, providing a more accurate representation of the elemental composition of the algae from which the sample as taken. In some embodiments, the water wash is performed as part of algae harvesting within the biofuel production processes and the algae sample taken for elemental analysis is taken after the water wash.

A variety of effective water wash conditions can be used either in the production of biofuels or in preparing a sample for elemental analysis. A water wash can be performed in a batch, semi-batch, or continuous mode. Suitable effective pressures for the water wash include from a roughly ambient pressure (i.e., not pressurized relative to external environment, or no gauge pressure) or alternatively about 14 psig (0.1 MPag) up to about 2500 psig (17.2 MPag). Examples of pressure for operation include a low pressure from about ambient or alternatively about 14 psig (0.1 MPag) to about 100 psig (0.7 MPag). Another option is to operate at a medium pressure from about ambient or alternatively about 14 psig (0.1 MPag) up to about 500 psig (3.4 MPag), such as from about 100 psig (0.7 MPag) to about 300 psig (2.1 MPag). Still another option is to operate at a high pressure from about ambient or alternatively about 100 psig (0.7 MPag) up to about 2500 psig (17.2 MPag), such as from about 300 psig (2.1 MPag) to about 2000 psig (13.8 MPag), from about 300 psig (2.1 MPag) to about 1700 psig (11.7 MPag), or from about 500 psig (3.4 MPag) to about 1000 psig (6.9 MPag). If a gas is added to a reaction system to achieve the desired pressure during the water wash, an inert gas such as $N_2$ may optionally be used. Suitable effective temperatures for the water wash may include from about 20° C. (or alternatively about ambient) to about 200° C., such as from 25° C. to about 150° C., from about 25° C. to about 100° C., from about 25° C. to about 80° C., from about 40° C. to about 80° C. In some embodiments, the temperature for the water wash may be from about 40° C. to about 60° C., or from about 40° C. to about 50° C.

The amount of time for exposing algae to the water wash can vary depending on the reaction conditions. Suitable effective times may include from about 1 minute to about 20 minutes, such as about 2 minutes to about 10 minutes. The amount of water used in the water wash can also vary. In a batch type configuration, the weight of water used for the water wash may be comparable to the weight of the algae sample or algae feed, such as a ratio of wash water to algae of about 1:2 to about 3:1. The wash water can be removed from the algae by any suitable means, such as using a pressure differential to remove water from the processing vessel or centrifugation. At low ratios of wash water to algae, the amount of wash water may be less than the amount of water already present in the algae sample.

In a configuration where the wash water has a continuous flow, it may be advantageous to use larger ratios of wash water to algae. A relatively low amount of desired products are expected to be removed in the water wash, so that product recovery does not need to be performed on the wash effluent, and a larger flow of water will pose fewer problems. Suitable weight ratios of wash water to algae sample may include from about 1:2 to about 5:1.

The composition of the effluent from the water wash process will vary depending on the water wash conditions. Under typical conditions, such as a pressure of 100 psig (0.7 MPag) or less, the effluent will primarily contain water soluble salts such as NaCl.

If a water wash is performed, at least a portion of the effluent can optionally be recycled for further use. The recycling use and processing before or during recycling can depend on the composition of the wash effluent. For a wash effluent that primarily contains water and ionic salts, the wash water can be recycled to the growth environment. Further processing of a wash effluent prior to recycling can reduce or mitigate potential modifications of the conditions within the growth environment due to recycling, such as supplying an organic compound that may cause heterotrophic or mixotrophic metabolic changes in an algal culture intended to be photoautotrophic, or supplying an organic compound that may support the growth of deleterious organisms.

Sample Preparation

Algae samples can be prepared for analysis by removing water before elemental analysis, because water could incorrectly increase the oxygen percentage in the analysis. Dewatering or drying of algae may be accomplished by any suitable method including: sunlight, froth flotation, settling tanks, rotary dryers, flash dryers, vacuum dryers, ovens, freeze dryers (lyophilizer), hot air dryers, microwave dryers, superheated steam dryers, flocculation, centrifugation, filtration, or combination(s) thereof. For example, flocculation may be combined with centrifugation or filtration to improve the dewatering of the algal biomass.

In some embodiments, dewatering can be achieved by filtration, for example by membrane filtration. In this method, water permeates through the membranes and the algae become more concentrated on one side of the membranes. Typically, the membranes operate under a slight vacuum induced by a permeate pump, which pumps away water that flows through the membrane. Compressed air may be fed to the bottom of the membrane module to prevent solids from accumulating on the outside surface of the membranes. The air also provides agitation that keeps the algae suspended. Permeate water is also periodically pumped in reverse (from the inside to the outside of the membrane) to remove particles that may be lodged in the membrane interstices.

Additionally, dewatering may be accomplished by centrifugation. A centrifuge uses rotation around a fixed axis to generate centripetal acceleration resulting in the separation of materials based on density. Separation using centrifugation can be accomplished in a batch or continuous process. Typically, a continuous process is used for large volumes. In some embodiments, a disc stack centrifuge is used. In other embodiments, a decanter centrifuge is used. Disc stack and decanter centrifuges are commercially available from a number of manufacturers. Centrifugation may be applied to untreated material or used in combination with additional dewatering processes such as flocculation and/or filtration. By way of example, material may be first subjected to flocculation followed by centrifugation of the flocculants resulting in biomass having a water content of about 90% or less, such as about 80% or less, about 75% or less, about 70% or less, about 65% or less, or about 60% or less. Water content is defined as the weight % of water in a sample divided by the weight of the entire sample.

One method of increasing the concentration of algae is to flocculate or aggregate the organisms to facilitate removal from the aqueous environment. Flocculants or flocculating agents promote flocculation by causing colloids and other suspended particles (e.g., cells) in liquids to aggregate, forming a flocculant. Flocculants are used in water treatment processes to improve the sedimentation of small particles. For example, a flocculant may be used in swimming pools or drinking water filtration to aid removal of microscopic particles which would otherwise cause the water to be cloudy and which would be difficult to remove by filtration alone. The use of flocculants before elemental analysis may affect the results of such an analysis and have to be accounted for in the normalization process by subtracting out the elemental composition of the flocculant from the normalized elemental analysis.

Many flocculants are multivalent cations such as aluminum, iron, calcium or magnesium. These positively charged molecules interact with negatively charged particles and molecules to reduce the barriers to aggregation. In addition, many of these chemicals, under appropriate pH and other conditions such as temperature and salinity, react with water to form insoluble hydroxides which, upon precipitating, link together to form long chains or meshes, physically trapping small particles into the larger flocculant.

Long-chain polymer flocculants, such as modified polyacrylamides, are commercially available. These are supplied in dry or liquid form for use in the flocculation process. An example flocculant, liquid polyacrylamide, is typically supplied as an emulsion with 10-40% actives and the rest is a carrier fluid, surfactants and latex.

An alternative to chemical flocculation is biological flocculation. Biological flocculation has minimal to no effect on the elemental analysis and does not have to be considered in the normalization. However, biological flocculation may reduce the overall lipid or biofuel yield because some energy must be expended by the algae to produce the flocculant markers, energy that could have contributed to additional growth. In biological flocculation, the algae may be genetically engineered to produce one or more flocculation moieties on its surface. The flocculation moieties can be expressed constitutively or expression can be induced, for example, by the use of an inducible promoter. The flocculation moiety can be, for example, a carbohydrate or protein binding moiety that binds to a surface protein or carbohydrate located on the external surface of the algae. In such a case, expression of the flocculation moiety causes the algaes to bind to each other to form a flocculant. In other non-limiting examples the population of algaes contains subpopulations of microorganisms that have been genetically engineered to express complementary flocculation moieties on their surfaces, for example a carbohydrate binding lectin and its corresponding carbohydrate or an antibody and its corresponding antigen. Flocculation can be induced by growing the two populations separately and then mixing the populations, or alternatively, inducing expression of one or both of the molecules involved in flocculation. In another example, an organism that is genetically modified to produce and secrete a flocculation moiety can be used. Further examples of biological flocculation can be found in U.S. Pat. No. 8,969,006.

Physical methods for water removal, such as centrifugation, filtration, flocculation, or dissolved air flotation can be used to increase the algae content of an algae feed. For some algae strains, physical methods can increase the algae content up to about 20 wt % to 30 wt % solids. For other algae strains that are more difficult to process, physical water separation may only increase the algae content up to about 10 wt % solids. Increasing the solids (algae) content beyond 10 wt % solids may involve additional water removal techniques, such as heating to cause evaporation, or lyophilization.

Because algae include water within the cells, the cells are typically lysed to reduce water content to a desired level. Many of the drying techniques eventually cause destruction of the cell membrane, and allow for escape of much of the water content. Since analysis may be performed on small samples, it may be advantageous to freeze-dry (lyophilize) the sample. Lyophilization causes rupture of cellular membranes as the water within the cells freezes, and allows for reduction or elimination of water content within an algae sample. Elemental analysis does not involve large samples and therefore the energy and time needed to perform drying in such a manner is not prohibitive.

While lyophilization may be performed on the crude algae sample, dewatering is often included in industrial biofuel production from algae and, therefore, it may be advantageous to take the sample from the algal biomass after dewatering has been performed. Doing lyophilization after dewatering may decrease the overall cost in energy consumption and reduce the time to dry the sample.

In some embodiments, an algae sample is subject to lyophilization after dewatering. The algae sample used in the lyophilization may contain at least about 50 wt %, at least about 60 wt %, at least about 70 wt %, at least about 80 wt %, at least about 85 wt %, at least about 90 wt %, at least about 95 wt % or at least about 99 wt % water. During the lyophilization, the biomass is cooled to a lyophilization temperature from about −100° C. to about 0° C. In some embodiments, the lyophilization temperature is from about −80° C. to about −10° C., such as from about −80° C. to about −20° C., or from about −78° C. to about −40° C. The material may be held at the lyophilization temperature for any suitable period of time depending on the water content of the sample. Typical times include from about 5 minutes to about 96 hours. In some embodiments, the algae sample is held at the lyophilization temperature from about 10 minutes to about 72 hours, such as from about 1 hour to about 48 hours, or from about 12 hours to about 36 hours. Additionally, lyophilization may be accomplished at reduced pressures, such as from about 1 Pa to about 611 Pa, from about 10 Pa to about 600 Pa, from about 100 Pa to about 500 Pa, or from about 200 Pa to about 400 Pa. Typically, the temperature in a lyophilization is cycled to improve sublimation rate of ice present during lyophilization.

Equivalent lyophilization may be obtained with various combinations of time, pressure, and temperature. For example, as pressure is decreased, the amount of drying time may decrease. Lyophilization of algae sample may reduce the water to a content of about 10 wt % or less, such as about 5 wt % or less, 3 wt % or less, or about 1 wt % or less. Because some water may still remain, the lyophilized algae sample may undergo secondary drying.

After lyophilization is complete, and all ice has sublimed, bound moisture may still be present in the product. The product appears dry, but the residual moisture content may be as high as 7-8 wt % and continued drying at warmer temperature may reduce the residual moisture content to optimum values for elemental analysis. A secondary drying process may include Isothermal Desorption. Isothermal Desorption is defined as temperature induced desorption of bound water from the product. Secondary drying is normally continued at a temperature higher than ambient but compatible with the sensitivity of the algae sample. In contrast to processing conditions for lyophilization which use low temperature and a moderate vacuum, desorption drying is facilitated by raising temperature and reducing pressure. The increase in temperature is moderated by concern for degradation of the sample, and care should be exercised in raising shelf temperature too high; since, protein polymerization or biodegradation may result from using high processing temperature during secondary drying. Secondary drying is usually carried out for approximately ⅓ or ½ the time used in lyophilization.

Typically, secondary drying includes higher temperatures and lower pressures than lyophilization. For example, secondary drying may be performed at a temperature of from about 20° C. to about 120° C., such as from about 30° C. to about 100° C., from about 40° C. to about 80° C., or from about 50° C. to about 70° C. Additionally, secondary drying may be performed at a pressure of about 0 Pa to about 500 Pa, such as from about 1 Pa to about 200 Pa, or from about 10 Pa to about 100 Pa. Secondary drying is based on the assumption that ice is no longer present and remaining water is bound requiring increased energy for removal.

Following lyophilization and optionally secondary drying, the dried algae sample may be stored. The dried sample may be stored for any suitable period of time, such as from 1 day to 1 year. For example, the dried algae sample may be stored from 1 day to 1 month, from 1 month to 3 months, from 3 months to 6 months, from 6 months to 9 months or from 9 months to 12 months. The dried algae sample may be stored at ambient temperature or at a controlled temperature. If the dried algae sample is stored at a controlled temperature, the storage temperature may be from about 0° C. to about ambient temperature. In certain embodiments, the storage temperature can be from about −20° C. to about 25° C., such as from about −10° C. to about 20° C., from about −5° C. to about 20° C., from about 0° C. to about 20° C., from about 0° C. to about 15° C., or from about 0° C. to about 10° C.

Sample Analysis

Carbon, Hydrogen and Nitrogen (CHN) analysis may be performed by Dynamic Flash Combustion. In Dynamic Flash Combustion, samples are held in a suitable container (e.g, tin container), placed inside a drum (e.g., an autosampler drum) where the samples are purged with a continuous flow of helium and then dropped at preset intervals into a combustion reactor (e.g., a vertical quartz tube) maintained at a suitable temperature (e.g., about 600° C. to about 1,100° C., such as about 900° C.). In some embodiments, the combustion reactor may be maintained at a temperature of about 800° C. or higher, such as about 900° C. When the samples are provided to the inside of the combustion reactor, a helium stream is temporarily enriched with pure oxygen and both the sample and the sample's container melt. The tin promotes flash combustion in the temporary oxygen enriched atmosphere. Under these conditions, even thermally resistant substances are completely oxidized. Quantitative combustion is achieved by passing the mixture of gases over a copper catalyst layer to remove the excess of oxygen and to reduce the nitrogen oxides to elemental nitrogen.

The resulting mixture is directed to a chromatographic column, such as porapak PQS, where the individual components are separated and eluted as Nitrogen ($N_2$), Carbon dioxide ($CO_2$), Water ($H_2O$). The eluted products are quantitatively measured using a thermal conductivity detector. The thermal conductivity detector feeds a signal to a workstation for data interpretation. The instrument is calibrated with the analysis of standard compounds, such as EDTA or Aspartic Acid. All results for elemental analyses are calculated based on a known value of the standard by using the K value factors calculation. K values are determined by analyzing organic standards of a known elemental composition.

In some embodiments, the dynamic flash combustion is performed on an automated instrument, such as Thermo Flash 2000 Elemental Analyzer for CHN. Typically, dynamic flash combustion follows the methods described in ASTM D5291.

Oxygen Analysis can be performed according to the following method: The sample is weighed into a silver capsule that is folded and crushed to contain the sample and reduce or eliminate contributions from atmospheric oxygen. An autosampler is used to introduce the prepared capsule into the pyrolysis reaction tube that contains nickel-coated carbon. The pyrolysis reaction tube may be maintained at a temperature of 1000° C. or higher, such as about 1060° C. The purpose of the nickel/carbon catalyst, which is maintained at temperature of 1060° C. in a helium atmosphere, is to convert most of (e.g., substantially all or all) of the oxygen in the sample into CO. The CO produced is swept out of the reaction tube and through a short-path gas chromatography (GC) column. The GC column separates the CO from the other pyrolysis gases and detection is by a thermo conductivity detector. Quantification of the oxygen is accomplished by comparing detector response to an external calibration of the detector prepared using known oxygen standards. The pyrolysis reaction is performed on an automated instrument, such as Thermo Flash 2000 Elemental Analyzer for oxygen.

Further discussion of oxygen analysis may be found in ASTM D5622—Standard Test Methods for Determination of Total Oxygen in Gasoline and Methanol Fuels by Reductive Pyrolysis, incorporated by reference.

The combination of CHN and oxygen analysis gives a quantitative amount of each of those elements. The quantitative amounts of the elements are used again to normalize the amounts of all other elements.

X-Ray Fluorescence Analysis

X-ray fluorescence (XRF) spectroscopy may provide comparative amounts of elements. For example, XRF analysis of a sample may provide relative ratios of nearly every element on the periodic table within a sample.

A known amount of sample is prepared for the XRF analysis. The preparation may include milling the sample to a uniform size and mixing the milled sample using a non-contaminating vial and mixing balls with a shaker box. The preparation may include other methods of preparing a homogenous sample, e.g. a sample with comparable grain size. When practical, larger samples are used to reduce or eliminate questions of sample homogeneity.

The prepared sample is placed in an X-ray beam spectrometer. Suitable X-ray beam spectrometers are commercially available, such as Bruker S8 Tiger XRF or Malvern Panalytical Zetium XRF. Spectra are collected from scans across the appropriate wavelengths and instrument conditions for the characteristic energy of multiple lines for each element where possible. A net intensity ratio is calculated and converted to concentration using the prepared internal fundamental parameters calibration. The net intensity ratio is the ratio of the elements scanned based on the intensity of the emission of fluorescent x-ray from each element. These calibrations are based on a wide variety of matrix standards analyzed by the manufacturer and provided as a master Line Library at installation of the instrument. Any suitable XRF instrument may be used, such as a Bruker S8 Tiger XRF instrument can be used for this work where the samples may be measured under the helium mode with a 3 KW (Kilo-Walt) x-ray tube of rhodium (Rh) target.

The translation of X-ray photon count-rates into elemental concentrations can include: wavelength dispersive spectrometers (WDX) separate the X-ray lines efficiently, and the rate of generation of secondary photons is proportional to the element concentration. However, the number of photons leaving the sample is also affected by the physical properties of the sample's "matrix effects". Matrix effects may be separated into three categories, including X-ray absorption, X-ray enhancement, and a particular sample's macroscopic effects.

All elements absorb X-rays to some extent. Each element has a characteristic absorption spectrum which consists of a "saw-tooth" succession of fringes, each step-change of which has wavelength close to an emission line of the element. Absorption attenuates the secondary X-rays leaving the sample. For example, a given concentration of aluminium in a matrix of iron gives only one seventh of the count rate compared with the same concentration of aluminium in a silicon matrix. Mass absorption coefficients are well known and can be calculated. However, to calculate the absorption for a multi-element sample, the composition is either known or the analysis is accomplished iteratively. In order to arrive at accurate mass absorption the concentration of elements not measured by XRF may be needed, such as the concentration of CHN and O that were previously measured.

An XRF analysis may utilize one or more of the following: (1) X-ray tube: Rh target or other suitable target, (2) Optical path: Helium 99.995% minimum purity for analysis of liquids/powders and vacuum for light elements in solids, (3) Crystal with appropriate d-spacing capable of measuring elements in the 20 range required, (4) Pulse Height Analyzer or other means of energy discrimination, (5) Analytical balance: capable of weighing to the nearest 0.1 mg, (6) Plastic vials: suitably sized to use for mixing and simple grinding of samples, and/or (7) Shaker/Mixer: capable of handling assorted sized vials. A suitable shaker/mixer is available from several sources including Spex SamplePrep, 203 Norcross Avenue, Metuchen, N.J. 08840.

For the materials used, an XRF analysis may utilize one or more of the following: (1) the chemicals can be reagent grade, and/or all water used can be distilled or deionized, (2) P-10 Ionization Gas: Counter gas for the flow proportional detector is a nominal blend of 90% Argon/10% Methane, e.g., available from Airgas East, 6990A Snow Drift Rd, Allentown Pa., (3) Quality Control Standard BR-STG2 Reference disk available from Bruker-AXS or any other reference disk of known elements and concentration, (NOTE: Quality Control disk or any reference disks which should be stable over the period of time involved for this task), (4) X-ray cells. Disposable plastic cells and window assembly accessories of a diameter suitable for the instrument being used for this procedure. X-ray cells are available from several sources including Chemplex® Industries, Inc.

2820 S. W. 42nd Avenue, Palm City, Fla. 34990-5573, (5) X-Ray Cell Window Film: ¼-mil polypropylene or other suitable window film which will absorb the least target radiation and have high chemical resistance to the material being analyzed. The film is available from several sources including SPEX Sample Prep., (6) Polystyrene vials and methyl methacrylate ball pestles: for planetary ball milling samples to a uniform size and homogeneity. The vials and balls are available from several sources including Chemplex® Industries, Inc., and/or (7) Puncturing Tool: A tool with a short, sharp steel point, such as an awl or vent-hole punch (Chemplex®) that, if needed, can be used to puncture the back of the sealed sample cup to relieve pressure.

For calibration and standardization, an XRF analysis may utilize one or more of the following: (1) No additional calibration is performed for the SPECTRAplus® Standardless method used by the Bruker system. The master calibration can be predefined in a Line Library established via reference disks supplied by the manufacturer at the time of installation. The SPECTRAplus® software automatically corrects for most matrix effects using predefined fundamental parameters for sample cup/film, specimen state, and composition. (NOTE: Appropriate standards can be utilized to create a specific program to analyze particular samples for a desired analyte subset.), (2) Drift Correction: The original reference disks should be periodically analyzed to correct natural spectrometer flux., and/or (3) Frequency: Drift corrections should be confirmed every six months and after any detector changes (e.g., changes of P-10 gas, flow detector windows, etc.), or quality control sample result issues. Line Library intensities should be within 20%, relative, of the previous intensities to be validated by the software. The analyst should address intensity changes of greater than 10%, relative. If the drift is greater than 20%, consult the manufacturer. (NOTE: A drift correction should be done for each sample mask and sample environment utilized for sample analysis (e.g., Helium, vacuum, 23 mm and 34 mm sample masks or whatever size is appropriate for the system being used)).

In some embodiments, an XRF analysis includes one or more of the following: (1) Preparing samples so as to ensure sample homogeneity, comparable sample grain size, etc. For example, mill catalyst pellets to a uniform size and mix using a non-contaminating vial and mixing balls with a shaker box, (2) Filling a prepared, tared X-ray cup and record the sample weight to the nearest 0.1 mg. Examining the cup to ensure sample window is taut and free of wrinkles. (NOTE: Whenever possible fill X-ray sample cups one-half to two-thirds of their capacity. However, it is possible to analyze considerably less when no additional sample is available. When practical, it is desirable to use the entire sample to help minimize questions of sample homogeneity.), and/or (3) Using the predefined SPECTRAplus® standardless program with appropriate atmospheric and measurement parameters, and scanning the samples.

For calculations, the Lachance-Traill method may be used to calculate the concentration of each element based on iterations of the scan data using relationships such as:

$$C_i = C_{oi} + m_i * I_i * [1 + \Sigma \alpha_{ij} * C_j]$$

where:

| | |
|---|---|
| $\alpha_{ij}$ = | the alpha coefficients |
| $I_i$ = | intensity of analyte of interest |
| $C_i$ = | concentration of analyte |

| | |
|---|---|
| Coi = | initial concentration of analyte |
| Cj = | concentration of matrix element j |
| mi = | Slope |

An XRF method can include entering the global properties for the SPECTRAplus® evaluation program EVAL, for example, the measurement method used; sample weight, in grams; sample chemistry and the diameter of the mask, in millimeters, used into the program. (NOTE: Defining the sample chemistry as oxides determines the concentration of secondary atoms stoichiometrically, e.g., oxygen in oxides.)

Spectral overlaps can be determined to avoid any false positive concentrations. By observing both the stored sample file and line library, the analyst can make decisions on the acquired spectra. Analytes can be reviewed and fixed to their appropriate level if necessary.

An XRF method can include changing or optimizing any physical or chemical attributes of the measured sample based on any previous knowledge regarding sample matrix, LOI, density, etc. An XRF method can include entering a sample matrix, the predominant chemical component, if known or force the sum of all concentrations to be 100%. Examples of sample matrices are $CH_2$, CHN, carbon, nitrogen, oxygen, etc. (NOTE: Sample matrix or light element makeup is important to the overall final concentrations observed if a mass balance of 100% is to be achieved. Sample matrix will have an effect on final concentration due to matrix absorption/enhancement. All practical possibilities should be investigated in the data workup when appropriate.)

An XRF method can include a Compton Calculation, where the program scans for the Rh Compton scatter in the sample analysis. Scatter is based on sample composition, and as average atomic number decreases in a sample, the Compton intensity will increase. A pragmatic predicted workup will provide a Compton scatter close to one. One should try to achieve a Compton value as close to one as possible.

For quality control, the performance of the instrument and/or method should be confirmed on a regular basis by analyzing a QC standard at a scheduled frequency. The scheduled frequency may be set based on instrument usage and/or sample load. Typically, the QC disk can be checked on a monthly basis to verify program performance.

Further discussion of XRF analysis may be found in US Patent No. US20070196925A1, incorporated by reference.

Normalization

Because XRF analysis involves concentration of some elements to provide accurate estimation of total elemental composition, the XRF data is normalized based on the amount of CHN and O in the sample. The normalization may be accomplished by summation of the weight % of the C, H, N, and O ($\Sigma_{CHNO}$) in the sample and separate summation of the remaining elements ($\Sigma_{other}$). Then the weight percent (wt %) of an individual element can be determined using the formula (I):

$$\text{Actual wt \%} = XRF \text{ determined wt \%} * (100 - \Sigma_{CHNO}) / \Sigma_{other} \quad (I)$$

After each element is normalized the composition of the sample is known. The compositional data provides research insight into the amounts and ratios of lipid, protein, and carbohydrates formed in the algae strains. For example, a high nitrogen to carbon ratio suggests that the algae is producing more protein than lipid. Additionally, a high oxygen to carbon ratio suggests that the algae is producing more carbohydrate than lipids. Because lipids are often the source of biofuels, such as biodiesel, the use of elemental analysis may provide researchers the information to make decisions about algae growth conditions. The growth conditions, such as light intensities, feedstocks, temperature, and time may affect the ratios of proteins, carbohydrates, and lipids allowing for improved production of desired products.

Furthermore, elemental analysis may provide metal, salt, and/or sulfur content which can be accounted for during refining processes. For example, algae grown in salt water may have a higher salt content, and refinery feedstocks with high salt content are often desalted before being subject to other refinery processes where the salt may corrode equipment. Therefore, rapid and accurate elemental analysis is advantageous to production of biofuels in both algae growth and refining processes.

Types of Algae

Algal sources for biofuels can include unicellular and multicellular algae. Examples of such algae can include a rhodophyte, chlorophyte, heterokontophyte, tribophyte, glaucophyte, chlorarachniophyte, euglenoid, haptophyte, cryptomonad, dinoflagellum, phytoplankton, and the like, and combinations thereof. In some embodiments, algae can be of the classes Chlorophyceae and/or Haptophyta. Specific species can include: *Neochloris oleoabundans, Scenedesmus dimorphus, Euglena gracilis, Phaeodactylum tricornutum, Pleurochrysis carterae, Prymnesium parvum, Tetraselmis chui, Nannochloropsis gaditiana, Dunaliella sauna, Dunaliella tertiolecta, Chlorella vulgaris, Chlorella variabilis,* and *Chlamydomonas reinhardtii*. Additional or alternate algal sources can include one or more microalgae of the *Achnanthes, Amphiprora, Amphora, Ankistrodesmus, Asteromonas, Boekelovia, Borodinella, Botryococcus, Bracteococcus, Chaetoceros, Carteria, Chlamydomonas, Chlorococcum, Chlorogonium, Chlorella, Chroomonas, Chrsosphaera, Cricosphaera, Crypthecodinium, Cryptomonas, Cyclotella, Dunaliella, Ellipsoidon, Emiliania. Eremosphaera, Ernodesmius, Euglena, Franceia, Fragilaria, Gloeolhamnion, Haematococcus, Halocafeteria, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Phaeodactylum, Phagus, Platymonas, Pleurochrsis, Pleurococcus, Prototheca, Pseudochlorella, Pyramimonas, Pvrobotrys, Scenedesmus, Skeletonema, Spyrogyra, Stichococcus, Tetraselmis, Thalassiosira, Viridiella,* and *Volvox* species.

Biofuels or algal lipids are typically contained in algae in the form of membrane components, storage products, and metabolites. Certain algal strains, such as microalgae such as diatoms and green algae, contain proportionally high levels of lipids. Algal sources for the biofuels can contain varying amounts, e.g., from 2 wt % to 40 wt % of lipids, based on total weight of the biomass itself. The elemental analysis provides researchers with a method to compare algal strains in their production of lipids and biofuels.

Other Embodiments

The present disclosure provides, among others, the following aspects, each of which may be considered as optionally including any alternate aspects.

Clause 1. A method for compositional analysis of an algae sample, the method comprising:

flash combusting a first portion of the algae sample to provide a carbon wt %, a hydrogen wt %, and a nitrogen weight %;

pyrolysing a second portion of the algae sample to provide an oxygen wt %;

scanning a third portion of the algae sample using x-ray fluorescence to provide an elemental intensity; and normalizing the elemental intensity using the carbon wt %, the hydrogen wt %, the nitrogen wt %, and/or the oxygen wt %.

Clause 2. The method of Clause 1, further comprising drying the algae sample.

Clause 3. The method of Clauses 1 or 2, wherein the drying comprises lyophilizing the algae sample to form a lyophilized algae sample.

Clause 4. The method of any of Clauses 1 to 3, wherein lyophilizing is performed at a temperature of about −80° C. to about −20° C.

Clause 5. The method of any of Clauses 1 to 4, wherein lyophilizing is performed at a pressure of about 100 Pa to about 600 Pa.

Clause 6. The method of claim 3, wherein the drying further comprises secondary drying the lyophilized algae sample.

Clause 7. The method of any of Clauses 1 to 6, wherein the secondary drying is performed at a temperature of about 20° C. to about 100° C.

Clause 8. The method of any of Clauses 1 to 7, wherein the secondary drying is performed at a pressure of about 1 Pa to about 400 Pa.

Clause 9. The method of any of Clauses 1 to 8, wherein the flash combusting is performed at a temperature of about 900° C. or higher.

Clause 10. The method of any of Clauses 1 to 9, wherein the pyrolysing is performed at a temperature of about 1000° C. or higher in the presence of a nickel/carbon catalyst.

Clause 11. The method of any of Clauses 1 to 10, further comprising washing the algae sample with water before one or more of the flash combusting, the pyrolysing, or the scanning.

Clause 12. A method for compositional analysis of an algae sample, the method comprising:

drying the algae sample to produce a dried algae sample;

flash combusting a first portion of the dried algae sample to provide a carbon wt %, a hydrogen wt %, and a nitrogen weight %;

pyrolysing a second portion of the dried algae sample to provide an oxygen wt %;

scanning a third portion of the dried algae sample for elemental analysis using x-ray fluorescence; and normalizing the elemental intensity using the carbon wt %, the hydrogen wt %, the nitrogen wt %, and/or the oxygen wt %.

Clause 13. The method of Clause 12, wherein the drying comprises lyophilizing the algae sample to produce the dried algae sample.

Clause 14. The method of Clauses 12 or 13, wherein the lyophilizing is performed at a temperature of about −80° C. to about −20° C.

Clause 15. The method of any of Clauses 12 to 14, wherein the lyophilizing is performed at a pressure of about 100 Pa to about 600 Pa.

Clause 16. The method of any of Clauses 12 to 15, wherein the drying further comprises secondary drying.

Clause 17. The method of any of Clauses 12 to 16, wherein the secondary drying is performed at a temperature of about 20° C. to about 100° C.

Clause 18. The method of any of Clauses 12 to 17, wherein the secondary drying is performed at a pressure of about 1 Pa to about 400 Pa.

Clause 19. The method of any of Clauses 12 to 18, wherein the flash combusting is performed at a temperature of about 900° C. or higher.

Clause 20. The method of any of Clauses 12 to 19, wherein the pyrolysing is performed at a temperature of about 1000° C. or higher in the presence of a nickel/carbon catalyst.

Clause 21. The method of any of Clauses 12 to 20, wherein the dried algae sample has a water content of about 1 wt % or less.

Clause 22. The method of any of Clauses 12 to 21, further comprising washing the algae sample with water before one or more of the flash combusting, the pyrolysing, or the scanning.

EXAMPLES

General

A comparative analysis was performed using the technique described and compared to the previous technique of separating the algae crude into various fractions and then performing elemental analysis on individual fractions. In particular, fractions were analyzed separately and then combined results by their fraction weights. The recombined elemental composition largely matched that of direct analysis. The elemental balances validated that the method is quantitative and can be applied to analysis of biomass types with very different elemental compositions.

The algae was extracted using a soxhlet extractor first with heptane to produce the non-polar lipid fraction (Fraction 1) and second with 95% ethanol to produce the polar lipid fraction (Fraction 2). The insoluble material from the heptane and ethanol extraction were the salt fraction (Fraction 3) and the residual algae remaining in the soxhlet extractor was the Protein and Carbohydrate fraction (Fraction 4). The combination of fractions 1-4 provide an elemental analysis of the complete algae sample. Alternatively, a single sample was separated into portions for CHNO and XRF analysis. The data was normalized and produced results comparable to previous methods with substantially less time and effort involved.

| Element | Algae Crude from CHN + O and XRF Analysis Weight % | Algae Crude Combined Fractions 1-4 Weight % | Fraction 1: Non-Polar Lipids Weight % | Fraction 2: Polar Lipids Weight % | Fraction 3: Salts Weight % | Fraction 4: Proteins & Carbohydrates Weight % |
|---|---|---|---|---|---|---|
| H | 6.3 | 6.9 | 10.2 | 9 | 3.1 | 6.5 |
| C | 41.6 | 43.9 | 75.1 | 59.9 | 16.6 | 40.2 |

-continued

| Element | Algae Crude from CHN + O and XRF Analysis Weight % | Algae Crude Combined Fractions 1-4 Weight % | Fraction 1: Non-Polar Lipids Weight % | Fraction 2: Polar Lipids Weight % | Fraction 3: Salts Weight % | Fraction 4: Proteins & Carbohydrates Weight % |
|---|---|---|---|---|---|---|
| N  | 8.0  | 8.3  | 1.7  | 4.1  | 1.2  | 9.4  |
| O  | 27.3 | 31.4 | 11.6 | 23.7 | 9.4  | 33.8 |
| Na | 2.4  | 1.2  | 0.2  | 0.7  | 20.2 | 1.1  |
| Mg | 0.8  | 0.6  | 0.1  | 0.3  | 0.1  | 0.7  |
| P  | 2.6  | 1.9  | 0.3  | 0.4  | —    | 2.3  |
| S  | 1.2  | 0.9  | 0.1  | 0.1  | —    | 1.1  |
| Cl | 3.6  | 1.3  | 0.3  | 1.2  | 43.1 | 0.9  |
| K  | 2.6  | 1.4  | 0.2  | 0.3  | 6    | 1.6  |
| Ca | 0.8  | 0.5  | —    | —    | —    | 0.6  |
| Fe | 2.5  | 1.4  | —    | —    | —    | 1.7  |

Overall, it has been discovered that the combination of CHN and O elemental analysis performed via pyrolysis and x-ray fluorescence spectroscopy can provide a simple and efficient method for accurate elemental analysis of algae samples. The processes described are a dramatic improvement over prior methods of analyzing algae samples, which include many separations, evaporations, and individual analyses. The improved analysis methods may be applied to a variety of algae samples, including crude, lyophilized, soxhleted, and fractionated. The analysis provides elemental indicators for process controls and choice of algal strains in biofuel productions. Because the processes described are less time consuming than previous processes, the processes may be used in scale-up of biofuel production units.

The phrases, unless otherwise specified, "consists essentially of" and "consisting essentially of" do not exclude the presence of other steps, elements, or materials, whether or not, specifically mentioned in this specification, so long as such steps, elements, or materials, do not affect the basic and novel characteristics of this disclosure, additionally, they do not exclude impurities and variances normally associated with the elements and materials used.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, a range includes every point or individual value between its end points even though not explicitly recited. Thus, every point or individual value may serve as its own lower or upper limit combined with any other point or individual value or any other lower or upper limit, to recite a range not explicitly recited.

All documents described herein are incorporated by reference herein, including any priority documents and/or testing procedures to the extent they are not inconsistent with this text. As is apparent from the foregoing general description and the specific embodiments, while forms of this disclosure have been illustrated and described, various modifications can be made without departing from the spirit and scope of this disclosure. Accordingly, it is not intended that this disclosure be limited thereby. Likewise whenever a composition, an element or a group of elements is preceded with the transitional phrase "including," it is understood that we also contemplate the same composition or group of elements with transitional phrases "consisting essentially of," "consisting of," "selected from the group of consisting of," or "is" preceding the recitation of the composition, element, or elements and vice versa. The methods disclosed may be practiced in the absence of any element which is not disclosed herein.

While the present disclosure has been described with respect to a number of embodiments and examples, those skilled in the art, having benefit of this disclosure, will appreciate that other embodiments can be devised which do not depart from the scope and spirit of the present disclosure.

What is claimed is:

1. A method for compositional analysis of an algae sample, the method comprising:
    flash combusting a first portion of the algae sample to provide a carbon wt %, a hydrogen wt %, and a nitrogen weight %;
    pyrolysing a second portion of the algae sample to provide an oxygen wt % scanning a third portion of the algae sample using x-ray fluorescence to provide an elemental intensity; and
    normalizing the elemental intensity using the carbon wt %, the hydrogen wt %, the nitrogen wt %, and/or the oxygen wt %.

2. The method of claim 1, further comprising drying the algae sample.

3. The method of claim 2, wherein the drying comprises lyophilizing the algae sample to form a lyophilized algae sample.

4. The method of claim 3, wherein lyophilizing is performed at a temperature of about −80° C. to about −20° C.

5. The method of claim 4, wherein lyophilizing is performed at a pressure of about 100 Pa to about 600 Pa.

6. The method of claim 3, wherein the drying further comprises secondary drying the lyophilized algae sample.

7. The method of claim 6, wherein the secondary drying is performed at a temperature of about 20° C. to about 100° C.

8. The method of claim 7, wherein the secondary drying is performed at a pressure of about 1 Pa to about 400 Pa.

9. The method of claim 1, wherein the flash combusting is performed at a temperature of about 900° C. or higher.

10. The method of claim 1, wherein the pyrolysing is performed at a temperature of about 1000° C. or higher in the presence of a nickel/carbon catalyst.

11. The method of claim 1, further comprising washing the algae sample with water before one or more of the flash combusting, the pyrolysing, or the scanning.

12. A method for compositional analysis of an algae sample, the method comprising:

drying the algae sample to produce a dried algae sample;

flash combusting a first portion of the dried algae sample to provide a carbon wt %, a hydrogen wt %, and a nitrogen weight %;

pyrolysing a second portion of the dried algae sample to provide an oxygen wt % scanning a third portion of the dried algae sample for elemental intensity using x-ray fluorescence; and normalizing the elemental intensity using the carbon wt %, the hydrogen wt %, the nitrogen wt %, and/or the oxygen wt %.

13. The method of claim 12, wherein the drying comprises lyophilizing the algae sample to produce the dried algae sample.

14. The method of claim 13, wherein the lyophilizing is performed at a temperature of about −80° C. to about −20° C.

15. The method of claim 14, wherein the lyophilizing is performed at a pressure of about 100 Pa to about 600 Pa.

16. The method of claim 15, wherein the drying further comprises secondary drying.

17. The method of claim 16, wherein the secondary drying is performed at a temperature of about 20° C. to about 100° C.

18. The method of claim 17, wherein the secondary drying is performed at a pressure of about 1 Pa to about 400 Pa.

19. The method of claim 12, wherein the flash combusting is performed at a temperature of about 900° C. or higher.

20. The method of claim 12, wherein the pyrolysing is performed at a temperature of about 1000° C. or higher in the presence of a nickel/carbon catalyst.

21. The method of claim 12, wherein the dried algae sample has a water content of about 1 wt % or less.

22. The method of claim 12, further comprising washing the algae sample with water before one or more of the flash combusting, the pyrolysing, or the scanning.

* * * * *